United States Patent [19]

Audry et al.

[11] Patent Number: 5,292,723
[45] Date of Patent: Mar. 8, 1994

[54] LIQUID NUTRITIONAL COMPOSITIONS COMPRISING SLOWLY ABSORBED GLUCIDES

[75] Inventors: Francis Audry, Creully; Daniel Evard, Vincennes; Etienne Grasset, Neuilly Sur Seine; Véronique Jaussan, Caen, all of France

[73] Assignee: Clintec Nutrition Company, Deerfield, Ill.

[21] Appl. No.: 846,382

[22] Filed: Mar. 5, 1992

[30] Foreign Application Priority Data

Mar. 13, 1991 [FR] France ................. 91 03042

[51] Int. Cl.$^5$ ............... A61K 31/715; A61K 9/08; A61K 31/195
[52] U.S. Cl. ..................... 514/58; 514/23; 514/60; 424/439; 424/442; 426/580; 426/601; 426/602; 426/606; 426/800; 426/801; 426/808; 426/810
[58] Field of Search ............. 514/23, 58, 60, 866; 424/439, 442; 426/580, 601, 602, 606, 800, 801, 808, 810

[56] References Cited

U.S. PATENT DOCUMENTS

| | | | |
|---|---|---|---|
| 3,861,293 | 1/1975 | Buffa et al. | 426/64 |
| 4,120,952 | 10/1978 | Cardon | 514/60 |
| 4,239,784 | 12/1980 | Guiraud et al. | 426/580 |
| 4,251,562 | 2/1981 | LeGrand et al. | 426/580 |
| 4,376,824 | 3/1983 | Hurst et al. | 435/94 |
| 4,407,821 | 10/1983 | Mendy | 514/52 |
| 4,520,017 | 5/1985 | Tunc | 514/54 |
| 4,731,246 | 3/1988 | Chaukin et al. | 514/60 |
| 4,921,877 | 5/1990 | Cashmere et al. | 514/866 |
| 5,171,603 | 12/1992 | Singer et al. | 426/580 |

*Primary Examiner*—Ronald W. Griffin
*Attorney, Agent, or Firm*—Hill, Steadman & Simpson

[57] ABSTRACT

Novel liquid nutritional compositions comprising a lipid fraction, a protein fraction and a specific combination of glucides useful as dietetics and therapeutics.

16 Claims, No Drawings

LIQUID NUTRITIONAL COMPOSITIONS COMPRISING SLOWLY ABSORBED GLUCIDES

STATE OF THE ART

Many products based on glucides used in dietetics or therapeutics and more particularly in therapeutic nutrition already exist on the market. These products possess a glucide fraction containing, in variable proportions, polymer poly-saccharides of glucose of variable molecular weight in the form of dextrin maltose, disaccharides (maltose, saccharose, lactose), mono-saccharides (glucose) and all these glucides are easily and quickly absorbed.

The usefulness of the ingestion of slowly absorbed sugars to avoid night-time hypoglycemias has already been demonstrated in the case of type 1 glycogen disease by Chen. et al., Cornstarch therapy in type 1 glycogen-storage disease., New England Journal of Medicine, 1984; Vol. 310, p 171 to 175. These authors used, however, raw, native starch, which is put in suspension extemporaneously. Treatment by heating was impossible because the slow sugar character was then lost.

OBJECTS OF THE INVENTION

It is an object of the invention to provide novel liquid nutritional compositions containing a slowly absorbed glucide fraction as a major amount of the total weight of the composition.

It is another object of the invention to provide an improved nutritional method.

These and other objects and advantages of the invention will become obvious from the following detailed description.

THE INVENTION

The novel liquid nutritional compositions of the invention are comprised of a lipid fraction, a protein fraction and a glucide fraction comprising at least both glucose polymers and slowly absorbed glucides.

Liquid nutritional compositions did not exist until now since it was known that slowly absorbed glucides such as modified starches or pectin gave rise after cooking in aqueous solutions to stable gels, which increased the viscosity of the compositions containing them and did not allow liquid compositions to be obtained which are more suitable for the nutritional use of products for example by digestive probe.

Glucose polymers means mainly dextrin maltoses and slowly absorbed glucides means products having a significantly lower glycemic index than glucose and than the glycemic indices published for normal constituents: i.e., dextrin maltose, disaccharides such as maltose, saccharose. The slowly absorbed glucides are glucides which bring about a slower and weaker glycemic response than socalled rapid glucides and this slower and weaker response results from a slower digestive absorption.

The slowly absorbed glucides can be for example modified starches or soluble fibers. Modified starches are currently widely used in the agro-food and pharmaceutical industry because of their functional properties. They allow stable gels to be obtained after cooking in aqueous suspension and the gelling properties and the viscosity are increased as a result. What generally is an advantages is, on the contrary, a disadvantage for the liquid compositions of the invention.

The modified starches might be slowly absorbed sugars, which is desirable for the invention, but the phenomenon of furthering the formation of viscous gels in aqueous solution is not compatible with the final nutritional use of the product. Contrary to the teaching of the prior art, applicants have tried to determine if nevertheless certain starches and manufacturing processes could permit the implementation of the invention.

A certain number of modified starches were selected to respond to the technological constraints, namely, to be included in a ready-to-use preparation which is liquid and able to sterilized in an industrial manner. For this, four functional criteria are indispensable: resistance to U.H.T. type heat treatment, that is retaining fluidity when hot, stable viscosity with pH and temperature variations, good solubility in water; and resistance to retrogradation and shearing.

Three modified starches were retained after these functional property studies, Cleargum CB 90 (Roquette Freres S.A.,), Snowflake 6090 (Cerestar S.A.) and Encapsol 855 (National Starch and Chemical S.A.,).

Among the soluble fibers, there can be mentioned, for example, pectin or certain other soya fibers. As indicated previously, pectin normally also has a gelling action in a complex solution during sterilization treatments by heating and increases the viscosity of finished ready-to-use products, and because of this, impedes the flow of nutritional products by digestive probe. It is for this reason that it is not at present used in sterilizable artificial nutritional products, which can be administered by probe, although the usefulness of soluble fibers, notably of pectin, has been emphasized by some authors. Pectin is, in fact, slowly metabolized by the colon and leads to an energy intake spread over 24 hours (Pomare et al.,: Carbohydrate fermentation in the human colon and its relation to acetate concentrations in venous blood, Journal of Clinical Investigation, 1985, Vol. 75, p. 1448 to 1454). The ingestion of soluble fibers is also recommended for patients suffering from sugar diabetes.

The present invention consisted of researching and testing various fibers and pectins to see if they meet the constraints of a liquid product, ready-to-use and sterilizable, and contribute to a nutritional effect.

The influence of various pectins and fibers on the rheological behaviour of the liquid product to be sterilized was studied. By physical and physico-chemical tests, fibers and pectins corresponding to the following criteria: low sensitivity to calcium ions, not forming gels in a slightly or moderately sugared medium and not giving a very firm gel at pH's of between 6.0 and 7.5 when the solution contains at least 60% sugars, and being compatible with glucose polymers such as modified starches after a sterilization treatment by heating were selected.

It is therefore also a very important and unexpected characteristic of the present invention to be able to contain starches and soluble fibers such as pectin and nevertheless undergo sterilization by heating and retain a viscosity of less than $0.05 \, kg \times m^{-1} \times sec^{-1}$ (50 centipoises). A particular subject of the present invention is compositions characterized in that they are in a stable sterilized ready-to-use form.

Contrary to the compositions of the prior art described notably by Chen. et al., the present invention allows the use of modified starches such as Cleargum CB 90. which can be sterilized without physical modification and therefore allows ready-to-use liquid compositions to be prepared. The degree of polymerization of Cleargum CB 90 was measured before and after sterilization by UHT (7 seconds at 150° C.). The results obtained by HPLC on an HPIC-AS6 column were as follows: absence of mono- and disaccharides and no detection of glucose polymers containing less than 11 molecules of this element.

Preferred compositions of the invention are compositions characterized in that the glucide fraction is 5 to 40% of the total weight.

The liquid nature of the compositions of the invention is very important and therefore their viscosity is less than $0.05 \text{ kg} \times \text{m}^{-1} \times \text{sec}^{-1}$ (50 Centipoises), preferably less than $0.03 \text{ kg} \times \text{m}^{-1} \times \text{sec}^{-1}$ (30 centipoises). Compositions which have retained a viscosity of less than $0.02 \text{ kg} \times \text{m}^{-1} \times \text{sec}^{-1}$ (20 centipoises) (measured by a Contraves Rheomat 108 apparatus at an ambient temperature of 20° C.) and which allow an optional administration by digestive probe, are also preferred.

Among the preferred compositions of the invention are the compositions in which the glucide fraction contains at least the following glucides: maltodextrins, modified starch and soluble fibers. More preferably, the compositions have a glucide fraction constituent with a glycemic index, measured in a healthy person, which is less than or equal to 70, and is at least 20% by weight of the total glucides present in the composition.

The glycemic index is determined by the method of Wolever, et al., The use of the Glycemic index in predicting the blood glucose response to mixed meals. American Journal of Clinical Nutrition, 1986, Vol. 43, p. 167 to 172. The increase of integrated glycemia during the two hours which follow the ingestion of the glucide studied is compared to that obtained after ingestion of the same quantity of glucose (base 100).

Such compositions can be created by the incorporation of modified starches such as Cleargum CB 90 which is provided as a nonlimitative example. Soluble fibers (for example pectin) can also be used. Preferably, in the compositions of the invention, the simple or complex glucides, derived or not from starch, are at least 50% of the energy intake (the basis of the calculation being 16.744 kilojoules/g (4 kcal/g) of glucides present in the composition.

The compositions of the invention cannot contain saccharose and a sweet taste is therefore obtained by using another sweetening product: i.e. monosaccharide such as fructose, a strong sweetener such as aspartame or acesulfame K.

Of course, the compositions of the invention can have all the necessary nutritional elements, other than glucide, in carefully worked out proportions. Thus, they can contain proteins providing 10 to 17% of the T.E.I. (total energy intake), vitamins (A, D, E, C, B1, B2, PP, B6, B12, folic acid, biotin, B5, Kl, choline). The compositions can also provide for the physiological needs of mineral elements.

They also contain a lipid fraction providing 20 to 40% of the T.E.I. which lipid fraction can have approximately the following composition (for 2.670 g of lipids):

| | |
|---|---|
| LEAR Rapeseed oil | 1.281 g |
| Medium chain triglycerides (MCT) | 0.670 g |
| Corn oil | 0.400 g |
| Soya lecithin | 0.188 g Glycerol |

-continued

| | |
|---|---|
| stearate | 0.131 g |

As an indication, if this 2.670 g of lipids is incorporated in the composition to provide 30% of the T.E.I., the lipid fraction will provide the following essential fatty acids:

| | |
|---|---|
| Linoleic acid | 6.4% of the T.E.I. |
| Alpha-linolenic acid | 1.6% of the T.E.I. |

This lipid composition composition allows a sufficient quantity of esential fatty acids (8% of T.E.I.) to be provided and an alphalinolenic/linoleic acid ratio greater tha 1/10 to be retained.

The MCT's of the invention can be replaced by the following elements: olive oil or sunflower oil rich in oleic acid to increase the proportion of monounsaturated fatty acids, evening primrose oil rich in gamma-linolenic acid, synthetic triglycerides containing in position 1, 2 or 3 polyunsaturated fatty acids such as gammalinolenic acid (C18: 3, n-6), dihomogamma-linolenic acid (C20: 3, n-6), eicosapentaenoic acid (C20: 5, n-3).

The lipid fraction can particularly contain synthetic triglycerides corresponding to French Patent No 2,515,174, especially 1-3 dioctanoyl eicosapentaenoyl glycerol. Recent data suggests that the ingestion of eicosapentaenoic acid could have a beneficial effect in the therapeutics of patients who have insulin dependent diabetes (Jensen et al.,: Partial normalization by dietary cod-liver oil of increased microvascular albumin leakage in patients with insulin dependent diabetes and albuminuria. New England Journal of Medicine 1989, Vol. 321, p. 1572 to 1577), LEAR rapeseed oil to increase the intake of alpha-linolenic acid, corn or soya oil to increase the intake of linoleic acid.

Particular compositions of the invention are ready-to-use liquid preparations intended for feeding by oral route or nutrition by digestive route of patients, adults or children suffering from glucide metabolism anomalies which makes them susceptible to excessive variations of glycemia (hypo- or hyperglycemia), especially sugar diabetes and intolerance to glucose. In addition, diseases characterized by the impossibility of supporting a prolonged fast because of an increased risk of hypoglycemia can benefit from the invention: glycogenoses, hypoglycemias of children through lack of substract(hypoglycemias recurrent with ketose).

The compositions can be used in dietetics, resuscitation and therapeutics and for the preparation of foods or food supplements corresponding to specific nutritional needs.

The compositions can be used when nutritional assistance is necessary, either because the ingestion of normal food has become impossible or insufficient due to the state of the patient, or as a supplement to normal food, for example as a collation in the middle of the morning and at bedtime, these examples not being limitative. The compositions are particularly useful in the case of glucide metabolism anomalies running the risk of an excessive variation of glycemia (hyper- or hypoglycemia) such as sugar diabetes, insulin-dependent or not, intolerance to glucose, sickness with foreseeable risk of hypoglycemia (hypoglycemia recurrent with ketose, hypoglycemia through lack of substrate, congenital anomalies of the glucide or lipid metabolism running an increased risk of hypoglycemia in the case of fasting.) They are also useful as a replacement for meals within the framework of a calorie-reduced diet for an overweight patient having diabetes or an intolerance to glucose and in combination with a neutral vehicle suitable for oral or enteral administration.

The novel method of the invention for supplying nutrients to a human in need thereof comprises administering to said patient a nutritionally effective amount of a liquid nutritional composition comprising a lipid fraction, a protein fraction and a glucide fraction comprising at least both glucose polymers and slowly absorbed glucides. The said compositions may be administered orally or enterally and as a food or a food supplement.

The novel process of the invention for the preparation of a liquid nutritional composition of the invention comprises forming an emulsion in aqueous phase with a lipid fraction and slowly absorbed glucides and admixing the latter with a water-soluble phase of a protein fraction and glucide phase comprised of glucose polymers and at least 20% by weight of slowly absorbed glucides. Preferably, the emulsion in aqueous phase contains 0.5% soluble fibers, preferably pectin. In a preferred embodiment, the resulting composition is sterilized and then homogenized.

In the following examples, there are described several preferred embodiments to illustrate the invention. However, it is to be understood that the invention is not intended to be limited to the specific embodiments.

EXAMPLE 1

The dietary and/or therapeutic liquid preparation for oral or enteral use for administration by digestive probe, was prepared with the following formula:

| Centesimal composition: | |
|---|---|
| 11.000 g of glucides consisting of | |
| Maltodextrins | 6 925 g |
| Cleargum CB 90 | 3.200 g |
| Fibers/pectins | 0.500 g |
| Lactose provided by the ingredients ingredient of the protein fraction | 0.375 g |
| (Acesulfame K | 15.000 g |
| 2.670 g of lipids consisting of | |
| MCT | 0.670 g |
| Corn oil | 0.400 g |
| LEAR rapeseed oil | 1.281 g |
| Soya lecithin | 0.188 g |
| Glycerol stearate | 0.131 g |
| 3.000 g of protein consisting of | |
| 75% lactoserum proteins | 2.750 g |
| Dried skimmed milk | 0.249 g |
| Carnitine | 2.500 mg | vitamins and minerals according to the tenth edition (1989) of RDAs (Subcommittee on the Tenth Edition of the RDAs, Food and Nutrition Board, Commission on Life Sciences, National Research Council: Recommended Dietary Allowances, 10th edition. National Academy Press, Washington D.C. 1989). water sufficient quantity for 100 ml. Manufacturing technique.

The preparation of 2500 liters of Example 1 was effected in a 3-stage process as follows:

The equipment used consisted of: a 400 liter mixer, a 4000 liter stainless steel vat equipped with an agitation system and a heating and cooling system, a plate heat exchanger with three circuits for cooling to 5° C., cooling to 15° C. and heating, 2 centrifuge pumps and a grinder.

| Constituents | |
|---|---|
| 1.- | |
| Pectin | 13.77 kg |
| Carragheenates | 500.00 g |
| Disodium phosphate | 500.00 g |
| Soya lecithin | 4.70 kg |
| Corn oil | 10.00 kg |
| LEAR rapeseed oil | 32.03 kg |
| M.C.T. | 16.75 kg |
| Glycerol stearate | 3.27 kg |
| Water that has undergone osmosis | 250.00 liters |
| 2.- | |
| Milk proteins | 68.73 kg |
| Water that has undergone osmosis | 900.00 liters |
| 3.- | |
| Maltodextrins | 180.30 kg |
| Dried skimmed milk | 17 50 kg |
| Modified starch | 89.30 kg |
| Acesulfame K | 375.00 g |
| Water that has undergone osmosis | 250.00 liters |
| Water that has undergone osmosis sufficient quantity for | 2500.00 liters |

The manufacturing process was as follows: 1 was dispersed in the mixer at 60° C., then mixed with 2. 1 and 2 were stirred for 2 minutes and the mixture wa emptied into the 4000 liter vat passing through the grinder. The temperature was lowered to 35° C., due to the cooling section of the exchanger and then 3 was incorporated successively into the mixer at a temperature of less than 40° C., working in a closed circuit (mixer-vat-exchanger-mixer). The mixture of 1, 2 or 3 was recirculated in a closed circuit for 5 minutes and then emptied completely into the 4000 liter vat.

A quantity of water that has undergone osmosis was introduced into the circuit to adjust the volume of the vat to 2450 liters. The density of the product of the vat and the adjustment by weight were measured by balances and the pH was adjusted to 7.10 by the addition of a 2N solution of potassium hydroxide. The mixture was then degassed, UHT sterilized and homogenized at a pressure of approximately 200 kg/cm$^2$ at 75° C. and finally distributed aseptically into sealed metal cans. The product was then stored at ambient temperature. Stability: no rising of fatty substance, nor creaming, nor gelling of the product was observed after 90 hours.

EXAMPLE 2

A dietary and/or therapeutic solution for oral or enteral use was prepared as in Example 1, except that the pectin was substituted by soya fibers and acesulfame K was replaced by fructose.

| Centesimal composition: | |
|---|---|
| proteins: milk proteins (N × 6.25) | 3.00 g |
| lipids: | 2.67 g |
| of which M.C.T. | 0.67 g |
| Corn oil | 0.40 g |
| LEAR rapeseed oil | 1.28 g |
| Soya lecithin | 0.19 g |
| Glycerol stearate | 0.13 g |

Clinical Study

A 375 ml can of the product of Example 1 was consumed daily by six diabetics of type II, two men and four women aged between 42 and 74 years (average: 60.5 years), overweight by 26.7% to 49.5% (average: 38.8%), for a period of 21 consecutive days in the hospital for 4 of them and a period of 28 consecutive days in an ambulant state for the other 2. Each can of the product provided 300 KCal, either as a substitute for breakfast for the 4 hospitalized patients, or as a partial substitute for lunch for the ambulatory patients. The 6 patients were put on a personalized calorie-reduced diet providing 4186 to 5860.4 kilojoules per day (1000 to 1400 Kcal) (average: 5023.2 kilojoules (1200 Kcal)). 1255.8 kilojoules (300 Kcal) of which was the product of Example 1. None of the 6 patients showed a digestive intolerance (no nausea, no vomiting, no diarrhoea, no anorexia), or extradigestive intolerance during this prolonged clinical trial.

Adherence to taking the product wa excellent: 375 ml of the product, 1255.8 kilojoules (300 Kcal), were effectively consumed daily by each of the 6 patients, for 21 days for 4 of them and for 28 days for the other 2. No appearance of anomalies in the make up of the blood, the liver examination (ASAT, ALAT, alkaline phosphates) the kidney function (presence of creatinine in the blood) or the plasmatic electrolytic balance (natremia, kaliemia, alkaline reserve) was noted in the 6 patients.

The weight loss of 0.4 to 5.2 kg, noted for the 6 patients (average: 2.7 kg), was accompanied by a lowering in 5 patients out of 6 of basal glycemia of 0.5 to 6 mmol/l (average: 3.8 mmol/l) and of post-prandial glycemia of 1.4 to 8.3 mmol/l (average: 3.4 mmol/l). In total, 375 ml of the product taken daily for 3 or 4 weeks by 6 diabetics of type II was perfectly tolerated both on a clinical and a biological level.

Various modifications of the compositions and method of the invention may be made without departing from the spirit or scope thereof and it is to be understood that the invention is intended to be limited only as defined in the appended claims.

What we claim is:

1. A liquid nutritional composition comprising a lipid fraction, a protein fraction and a glucide fraction comprising at least both glucose polymers and slowly absorbed glucides, wherein the fractions are selected such that the composition remains liquid after a heat treatment.

2. A composition of claim 1 in a stable, sterilized, ready-to-use form.

3. A composition of claim 1 wherein the glucide fraction is 5 to 40% by weight of the total weight.

4. A composition of claim 1 with a viscosity of less than $0.05 \text{ kg} \times \text{m}^{-1} \times \text{sec}^{-1}$ (50 centiposes).

5. A composition of claim 4 with a viscosity of less than $0.03 \text{ kg} \times \text{m}^{-1} \times \text{sec}^{-1}$ (30 centiposes).

6. A composition of claim 1 wherein the glucide fraction includes at least maltodextrins, modified staroh and soluble fibers.

7. A composition of claim 1 wherein the glucide fraction has a glycemic index of not more than 70, measured in a healthy person, and it is at least 20% by weight of the total glucides in the composition.

8. A food or food supplement containing a neutral vehicle for oral or enteral administration and a composition of claim 1.

9. A process for the preparation of a liquid nutritional composition comprising:
   forming an emulsion in aqueous phase with a lipid fraction and slowly absorbed glucides;
   admixing the latter with a water-soluble phase of a protein fraction and a glucide phase comprised of glucose polymers and at least 20% by weight of slowly absorbed glucides, wherein the fractions are selected such that the composition remains liquid after a heat treatment.

10. The process of claim 9 wherein the slowly absorbed glucides in the emulsion are soluble fibers.

11. The process of claim 10 wherein the soluble fibers are 0.5% by weight of the emulsion.

12. The process of claim 11 wherein the fibers are soluble fibers of pectin.

13. The process of claim 9 wherein the final mixture is sterilized and then homogenized.

14. A method of supplying nutrients to a human comprising administering orally or enterally a liquid nutrional composition of claim 1.

15. A liquid nutritional composition for providing nutrition to a patient with a metabolic abnormality due to the abnormal metabolism of glucide or lipid comprising a lipid fraction, a protein fraction and a glucide fraction comprising at least both glucose polymers and slowly absorbed glucides wherein the fractions are selected such that the composition remains liquid after a heat treatment.

16. A method for providing nutrition to a patient with a metabolic abnormality due to the abnormal metabolism of glucide or lipid comprising the step of administering to the patient a composition comprising a lipid fraction, a protein fraction and a glucide fraction comprising at least both glucose polymers and slowly absorbed glucides.

* * * * *